United States Patent [19]
Hechenbleikner et al.

[11] 3,939,229
[45] Feb. 17, 1976

[54] PREPARATION OF ALIPHATIC PHOSPHATES

[75] Inventors: Ingenuin Hechenbleikner, West Cornwall; William Planter Enlow, Falls Village, both of Conn.

[73] Assignee: Borg-Warner Corporation, Chicago, Ill.

[22] Filed: Dec. 4, 1974

[21] Appl. No.: 529,672

[52] U.S. Cl. .............................................. 260/985
[51] Int. Cl.² ...................... C07F 9/11; C07F 9/113
[58] Field of Search .................................... 260/985

[56] References Cited
UNITED STATES PATENTS 3,136,804   6/1964   Hodan et al. ...................... 260/985
3,333,030   7/1967   Baranauckas et al. .............. 260/985

Primary Examiner—Richard L. Raymond
Attorney, Agent, or Firm—Joseph Shekleton

[57] ABSTRACT

A process for the preparation of trialkyl and trialkenyl phosphates. The process involves oxidation of the corresponding phosphite with oxygen or an oxygen-containing gas. The oxidation is catalyzed by a metal catalyst such as a transition metal carboxylate, for example, and is carried out at relatively low temperatures.

7 Claims, No Drawings

PREPARATION OF ALIPHATIC PHOSPHATES

This invention relates to a process for the preparation of aliphatic phosphates by means of the oxidation of certain trialkenyl phosphites or trialkyl phosphites. More particularly, it relates to such a process which avoids high temperatures and yet results in very good yields.

The aliphatic phosphates made available by this invention are useful as plasticizers, gasoline additives, lubricant additives and flame-retarding additives. The trialkenyl phosphates are excellent cross-linking agents in the curing of ethylene polymers such as low density polyethylene or EPDM polymers.

The conversion of tertiary aliphatic phosphites to the corresponding phosphates via oxidation affords a convenient method of synthesis of these desirable products. They can also be prepared by the reaction of phosphorus oxychloride with the appropriate alcohol, in the presence of a hydrogen chloride scavenger like $NH_3$ or an amine, and this synthesis has been used, but it involves the elimination of large amounts of ammonium or amine hydrochloride which is both wasteful of chlorine, is corrosive, and is a disposal problem. The oxidation of phosphites is a preferred method.

Early oxidative methods of preparing tertiary phosphates involves treatment of the corresponding tertiary phosphites with air (Zimmerman, Ann. 175. 1 (1875) and with a combination of air and sulfur trioxide (Buchheim, U.S. Pat. No. 2,059,084). Later developments, as taught by Hechenbleikner in U.S. Pat. No. 2,851,476, involved the use of hydrogen peroxide in an aqueous alkaline medium, but this suffered from the disadvantage of hydrolysis of the phosphite (because of the presence of water), the high cost of hydrogen peroxide, and the need for careful control of pH.

Hodan et al., U.S. Pat. No. 3,136,804, and Baranauckas et al., U.S. Pat. No. 3,136,805, show the oxidation of trialkenyl and trialkyl phosphites, respectively, to the corresponding phosphates by the action of oxygen in an anhydrous medium, using a metal oxide such as aluminum oxide or vanadium oxide as a catalyst, yields of 88–96% are obtained and losses due to hydrolysis are avoided because of the absence of water in the oxidation mixture. The oxidations are carried out at temperatures between 60°C and 180°C, preferably between 100°C and 125°C, and for a period of time ranging from two to seven hours.

Similarly, Baranauckas et al., U.S. Pat. No. 3,333,030, show the oxidation of secondary phosphites such as dimethyl or diphenyl phosphite by means of oxygen in the presence of a catalyst such as copper or copper oxide. Many other metal catalysts are said to be effective also. The products are a mixture of the corresponding primary and secondary phosphates. Reaction temperatures are generally above 100°C, although slightly lower temperatures, down as low as 65°C, are also suggested.

Still another method of oxidizing tertiary olefinic phosphites to the corresponding phosphates by means of air is shown in Hodan et al., U.S. Pat. No. 3,334,158. The method involves a short residence time, i.e., less than 20 minutes and preferably less than 5 minutes, in the reaction zone. The temperature is above 100°C, preferably between 130°C and 190°C. The reaction zone is a column packed with protruded stainless steel.

All of these processes must be carried out at relatively high temperatures; some require rather careful and precise control of reaction conditions. Those which give best yields require more care than the others. A low temperature process which affords good yields of tertiary phosphate, with minimum required attention to process conditions, is desirable.

It is accordingly a principal object of the present invention to provide an improved process for preparing aliphatic phosphates.

Another object is to provide such a process which is effective at relatively low temperatures.

Still another object is to provide such a process which results in good yields of trialkyl or trialkenyl phosphates.

These and other objects are accomplished by a process for preparing aliphatic phosphates comprising contacting a trialkyl or trialkenyl phosphite with oxygen in the presence of a metal catalyst selected from the class consisting of transition metal, copper and tin catalysts, at a temperature of from about 20°C to about 60°C. Yields of tertiary phosphite are very good, i.e., virtually quantitative in most cases, and the process requires no unusual attention.

The trialkenyl or trialkyl phosphite may be defined in terms of a structural formula, as follows:

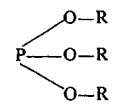

where R is alkyl, alkylenyl or alkenyl, each containing 1–20 carbon atoms. Illustrative alkyl groups include methyl, ethyl, n-propyl, isopropyl, n-butyl, isobutyl, n-amyl, sec-amyl, n-hexyl, isohexyl, 2-methylamyl-4, 2-ethylhexyl, n-octyl, isooctyl, n-dodecyl, n-tetradecyl, n-octadecyl, and eicosyl. Illustrative alkenyl radicals include allyl, methallyl, crotyl, pentenyl-2,3, 3-dimethallyl and 2,3-dimethallyl. The phosphite may be a mixed phosphite, i.e., one in which the alkyl or alkenyl groups are dissimilar. Illustrative alkylenyl groups include the residues from 1,3-octylene glycol, ethylene glycol, trimethylene glycol, glycol, 1,4-butane diol, 1,2-hexylene diol and 1,3-hexylene diol.

The oxygen may be used as such, i.e., without dilution, or it may be diluted, as in air. Ordinarily, the oxygen is bubbled into the phosphite, either neat or in a solvent, until the mixture is completely oxidized. This end point is shown by testing with iodine which is reactive with any unreacted phosphite, and a negative test indicates completion of the reaction.

Alternatively, the reactor vessel may be evacuated to about 5 mm. Hg and oxygen fed in on demand, i.e., oxygen is introduced only as fast as it is consumed by the oxidation reaction.

A solvent may be used but is not necessary. Heptane is a suitable solvent.

The metal catalyst is as indicated a catalyst in which the metal is a transition metal or copper or tin. Generally, the metal is present as an aliphatic carboxylate, although the chromium in a chromate salt has been found to be satisfactorily effective. Similar aliphatic carboxylates include octoates, decanoates, laurates, stearates, naphthenates and the like.

The process of the invention is illustrated by the following examples. All parts and percentages herein are by weight unless otherwise expressly stated.

EXAMPLE 1

To 10 ml. of an aqueous solution containing 0.5 g. of sodium carbonate and 0.25 g. of sodium bicarbonate there is added a solution of 1.0 g. of potassium dichromate in 50 ml. of water, then 60 ml. of triallyl phosphite. The resulting mixture is stirred at 25°–30°C while passing in oxygen for eight hours. The aqueous layer is removed, leaving a 96% yield of substantially pure triallyl phosphate.

EXAMPLE 2

A mixture of 0.2 g. of cobalt octoate and 70 g. of trioctyl phosphite is warmed in vacuo (10 mm.) at 30°C while oxygen is added over a period of six hours. The mixture is stirred throughout this period by means of a magnetic stirrer. The product is washed with an aqueous alkaline solution to remove the cobalt catalyst, having a 91% yield of trioctyl phosphate.

EXAMPLE 3

A mixture of 0.1 g. of copper octoate and 200 g. of triallyl phosphite is warmed in vacuo (10 mm.) at 25°–35°C while oxygen is added. The absorption of oxygen is monitored and when, after about four hours, the rate of absorption has fallen off to a substantially nothing, the reaction is halted and the product washed with aqueous alkali. The yield of triallyl phosphate is 92% of the theory.

EXAMPLE 4

The procedure of Example 2 is repeated using 0.01 g. of stannous neodecanoate as the catalyst instead of 0.1 g. of cobalt octoate and halting the reaction after four hours (instead of six hours). A 50% yield of trioctyl phosphate is obtained. Similar procedures using chromium octoate and copper octoate as the catalysts also yield trioctyl phosphate in 50% yield.

We claim:

1. A process for preparing aliphatic phosphates comprising contacting a trialkyl or trialkenyl phosphite with oxygen in the presence of a metal catalyst selected from the class consisting of chromium, copper, tin or cobalt catalysts, at a temperature of from about 20°C to about 60°C.

2. The process of claim 1 wherein the catalyst is a metal carboxylate.

3. The process of claim 1 wherein the catalyst is a metal salt of an aliphatic carboxylic acid.

4. The process of claim 1 wherein the phosphite reactant is a trialkenyl phosphite.

5. The process of claim 1 wherein the phosphite reactant is triallyl phosphite.

6. The process of claim 1 wherein the phosphite reactant is a trialkyl phosphite.

7. The process of claim 1 wherein the catalyst is a cobalt salt of an aliphatic carboxylic acid.

* * * * *